(12) United States Patent
Gallem et al.

(10) Patent No.: US 7,255,106 B2
(45) Date of Patent: Aug. 14, 2007

(54) INHALATION MASK

(75) Inventors: Thomas Gallem, Munich (DE); Andreas Lintl, Starnberg (DE); Patra Midelia, Karlsfeld (DE); Markus Mornhinweg, Diessen (DE)

(73) Assignee: Pari GmbH Spezialisten fur effektive Inhalation (DE)

( * ) Notice: Subject to any disclaimer, the term of this patent is extended or adjusted under 35 U.S.C. 154(b) by 299 days.

(21) Appl. No.: 10/159,963

(22) Filed: May 29, 2002

(65) Prior Publication Data
US 2003/0037788 A1 Feb. 27, 2003

(30) Foreign Application Priority Data
Jun. 1, 2001 (DE) ................. 101 26 808

(51) Int. Cl.
*A62B 18/10* (2006.01)
*A62B 18/02* (2006.01)
(52) U.S. Cl. .................. 128/207.12; 128/206.21
(58) Field of Classification Search .......... 128/200.14, 128/200.18, 200.23, 202.27, 203.12, 203.15, 128/203.29, 206.21, 206.24, 206.28, 207.12, 128/207.14, 207.16, 203.24, 207.18, 205.25, 128/205.24, 206.12, 206.15, 207.13
See application file for complete search history.

(56) References Cited

U.S. PATENT DOCUMENTS

| | | | |
|---|---|---|---|
| 3,519,012 A | * | 7/1970 | Van Patten ............... 137/102 |
| 3,796,216 A | | 3/1974 | Schwarz |
| 4,259,951 A | * | 4/1981 | Chernack et al. ...... 128/200.14 |
| 5,765,553 A | * | 6/1998 | Richards et al. ....... 128/203.29 |
| 5,816,240 A | * | 10/1998 | Komesaroff ........... 128/200.23 |
| 5,865,172 A | * | 2/1999 | Butler et al. ........... 128/203.12 |
| 5,954,049 A | * | 9/1999 | Foley et al. ........... 128/203.29 |
| 6,578,571 B1 | * | 6/2003 | Watt ...................... 128/200.14 |
| 2005/0066964 A1 | * | 3/2005 | Bathe .................... 128/200.14 |

FOREIGN PATENT DOCUMENTS

| | | |
|---|---|---|
| DE | 2 318 914 | 10/1974 |
| DE | 37 07 952 A1 | 9/1988 |
| DE | 42 12 259 C1 | 1/1993 |
| DE | 42 41 272 C1 | 6/1994 |
| DE | 44 38 512 A1 | 5/1996 |
| DE | 195 48 380 A1 | 7/1996 |
| DE | 297 00 093 U1 | 3/1997 |
| DE | 298 07 489 U1 | 7/1998 |
| DE | 198 17 332 A1 | 1/1999 |
| EP | 0 288 937 A2 | 11/1988 |
| EP | 0 427 474 A2 | 5/1991 |

* cited by examiner

*Primary Examiner*—Teena Mitchell
(74) *Attorney, Agent, or Firm*—Merchant & Gould, P.C.

(57) ABSTRACT

The invention describes an inhalation or breathing mask for therapeutic nebulisers, in which around a connecting socket 4 for the therapeutic nebuliser is arranged an exhalation valve consisting of exhalation openings and a flexible valve element. The exhalation openings 7 are formed by exhalation channels 8 and can be closed individually by closure devices, for example stoppers, in order to set a predefined exhalation resistance.

Figure 1:
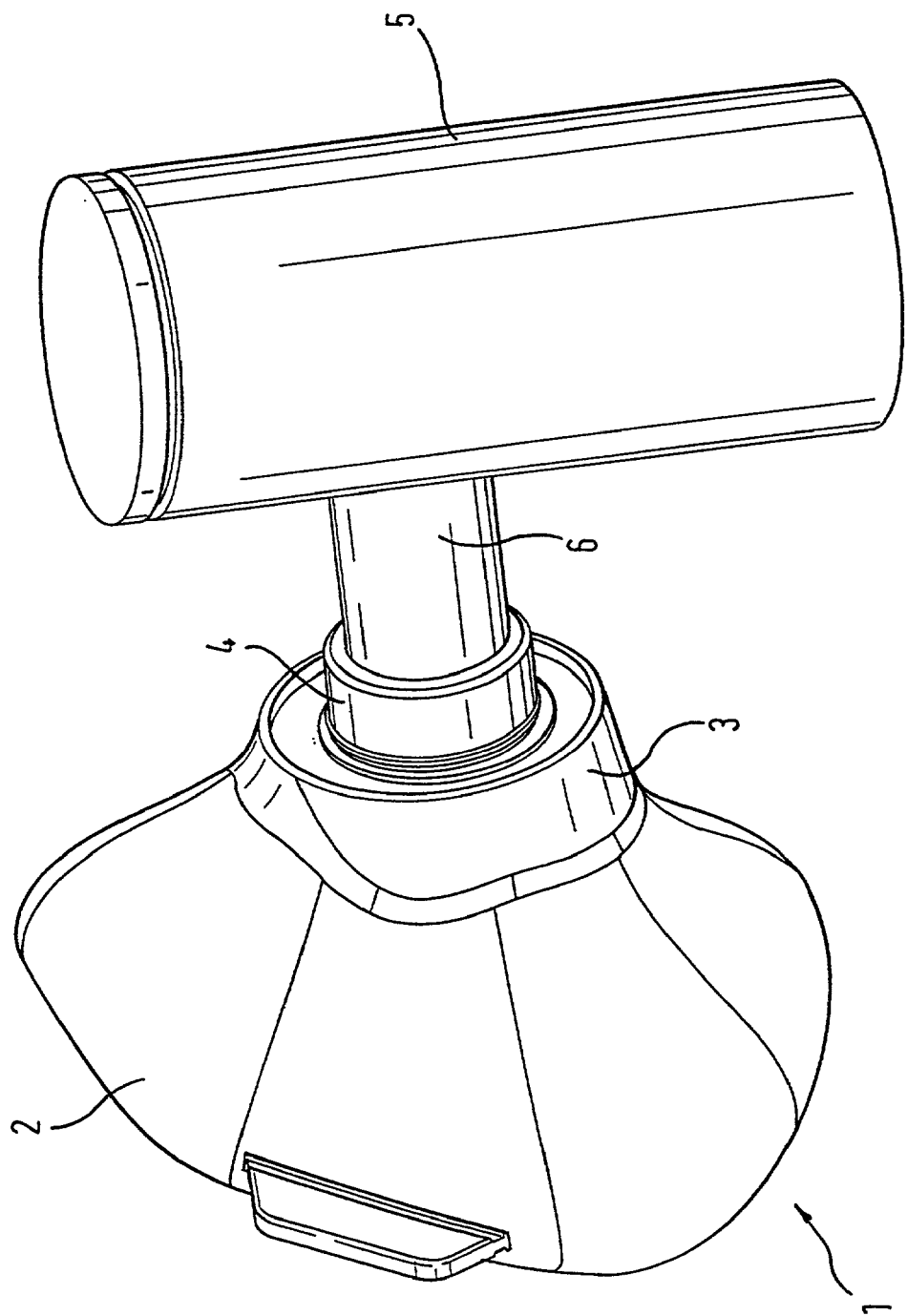
Figure 2:
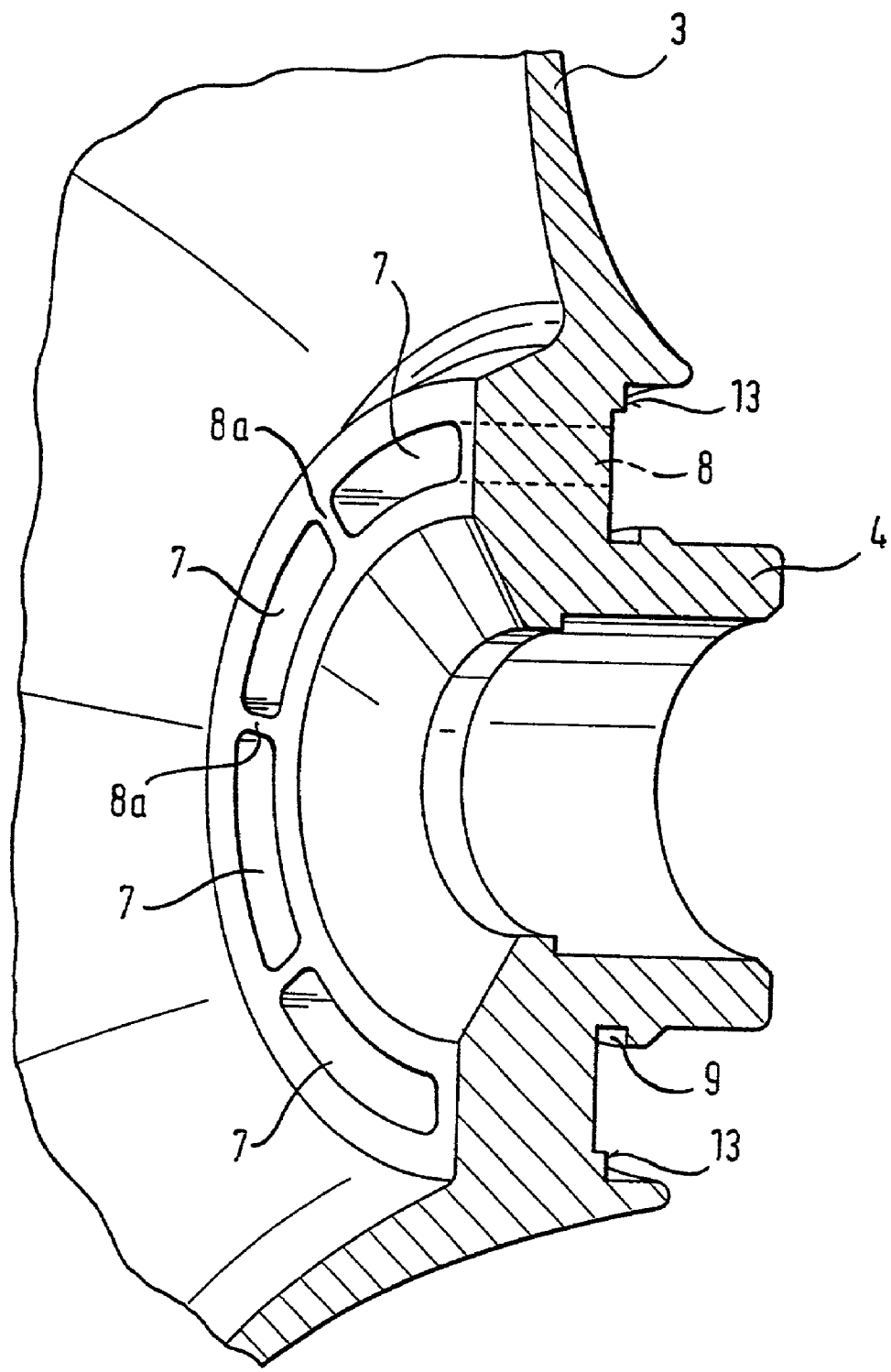

24 Claims, 9 Drawing Sheets

INHALATION MASK

FIELD OF THE INVENTION

The invention concerns an inhalation mask, in particular for use with a therapeutic nebuliser.

BACKGROUND

Nebulisers for therapeutic purposes, hereinafter referred to as therapeutic nebulisers, allow a user to inhale a drug-containing aerosol which was produced beforehand by an aerosol generator in the therapeutic nebuliser. To inhale the aerosol, the user usually takes a mouthpiece which is attached to the therapeutic nebuliser in his mouth and breathes in the aerosol through the mouthpiece. There are however groups of users for whom the use of a mouthpiece to inhale the aerosol is unsuitable or even impossible. For these groups of users, there are used inhalation or breathing masks which are put over the user's face so that the user can inhale the aerosol of the therapeutic nebuliser supplied via a connecting socket, as the aerosol is delivered to the mask via the connecting socket.

Traditional inhalation or breathing masks are of course appropriate solutions for the groups of users for whom the use of a mouthpiece is impossible or impracticable, but as a rule adversely affect the therapeutic quality. It may be supposed that, with inhalation or breathing masks for use with therapeutic nebulisers, improvements which have up to now not yet been exhausted are possible.

BRIEF SUMMARY

It is the object of the invention to show some of these improvements.

This object is achieved by an inhalation or breathing mask with the characteristics of patent claim 1. Advantageous embodiments are apparent from the subsidiary claims.

The invention is based on the finding that, for improving the therapeutic quality, it is important in particular to influence selectively the air flow which arises when the patient breathes out. This is achieved as a priority with the inhalation mask according to the invention by the arrangement and design of the exhalation valve. But alternatively, in addition, a further positive effect with respect to the therapeutic quality is obtained by influencing the effective cross-sectional area of the exhalation channels.

BRIEF DESCRIPTION OF THT DRAWINGS

Below, the invention is described in more detail with the aid of practical examples and with reference to the figures, which show:

FIG. 1 the overall view of an inhalation or breathing mask according to the invention;

FIG. 2 a perspective sectional view of the second mask region of an inhalation mask according to the invention;

FIG. 3 a sectioned view of the second mask region of an inhalation mask according to the invention; Image Page 1

FIGS. 4*a*, 4*b*, 4*c*, 4*d* sectioned views of the valve element of an inhalation mask according to the invention;

FIG. 4 sectioned views of the valve element of an inhalation mask according to the invention;

FIG. 5 a sectioned view of the second mask region of an inhalation mask according to the invention with an alternative valve element;

FIG. 6 a perspective sectional view of the second mask region of an inhalation mask according to the invention with closure devices;

FIG. 7 an alternative design of the closure device from FIG. 6;

FIG. 8 a perspective sectional view of the second mask region of an inhalation mask according to the invention with an alternative closure device; and FIG. 9 a perspective sectional view of the mask according to the invention as in FIG. 8 in another view.

DETAILED DESCRIPTION

FIG. 1 shows an inhalation or breathing mask according to the invention. It can be seen that the inhalation mask 1 can be roughly divided into a first mask region 2, which is designed for application of the mask to the user's face, and a second mask region 3 which according to the invention is equipped with a connecting device 4 for an inhalation therapy nebuliser 5, which is shown by way of example in the form of a nozzle nebuliser. An aerosol output connection 6 of the therapeutic nebuliser 5 is connected to the connecting socket 4. The aerosol produced in the therapeutic nebuliser is conducted via the aerosol output connection 6 to the connecting socket 4 and so passes into the interior of the mask 1 when the user wearing the mask breathes in.

FIG. 2 shows in a sectioned view the second mask region 3 of the inhalation mask according to the invention. The connecting device 4 for the therapeutic nebuliser (not shown) is in this embodiment a connecting socket with a basic cylindrical shape which is made from the material of the inhalation mask in one piece with the latter. The dimensions of the cylindrical connecting socket 4 are selected such that the latter offers sufficient grip to the inserted aerosol output connection of the therapeutic nebuliser.

Around the connecting socket 4 according to the invention are provided exhalation openings 7 through which the respiratory air of the user wearing the mask can flow out of the interior of the mask during exhalation. The exhalation openings 7 are, in the embodiment shown in FIG. 2, arranged concentrically around the cylindrical connecting socket 4. The number of exhalation openings 7 is selected so as to produce sufficient total cross-sectional area for the respiratory air of a user breathing out into the mask. The total cross-sectional area results from the sum of the cross-sectional areas of the breathing openings 7.

As shown in FIG. 2, the breathing openings 7 are formed by breathing channels 8 which extend through the material of the breathing mask essentially parallel to the longitudinal axis of the cylindrical connecting socket 4. Between the breathing channels 8 are formed connecting webs 8*a* which connect the connecting device 4 to the first mask region 2. Due to the fact that the connecting webs 8*a* extend in the direction of the longitudinal axis of the connecting device 4, the transition region between the first mask region 2 and the connecting device 4 is reinforced so that it can serve as the supporting core of the inhalation mask according to the invention and allows a correspondingly lightweight design of the first mask region 2.

As shown in FIG. 2, on the outside of the cylindrical connecting socket 4 in the immediate vicinity of the region 8 of the breathing channels is formed a peripheral groove 9. As shown in FIG. 3, in the groove 9 is inserted a valve element 10 which in the embodiment shown here is a flat annular disc which at its inner edge comprises a section 11 of enlarged cross-section. The section 11 is adapted to the groove 9, so that the valve element 10 is supported on the outside of the connecting socket 4. In this way the valve element 10 rests with its outer edge 12 on a supporting edge 13 which is formed in the breathing mask according to the invention, also running concentrically around the connecting socket 4. To prevent the valve element 10 from sticking, it is advantageous, by a sealing lip in the region of the supporting edge 13, in particular a prism-shaped sealing lip, to keep the area of contact between the valve element 10 and the mask in the region of the supporting edge 12 as small as possible. When the user wearing the breathing mask breathes in, the valve element 10 is moved with its outer edge 12 towards the supporting edge 13, so that the breathing openings 7 are closed. The user breathes in through the opening of the connecting socket 4 and hence through the aerosol output connection of the therapeutic nebuliser. When the user breathes out into the mask, the valve element 10 is lifted off the supporting edge 13, so that between the outer edge 12 of the valve 10 and the supporting edge 13 of the second mask region 3 forms a gap which clears the flow path for the exhaled air.

Figure 3:
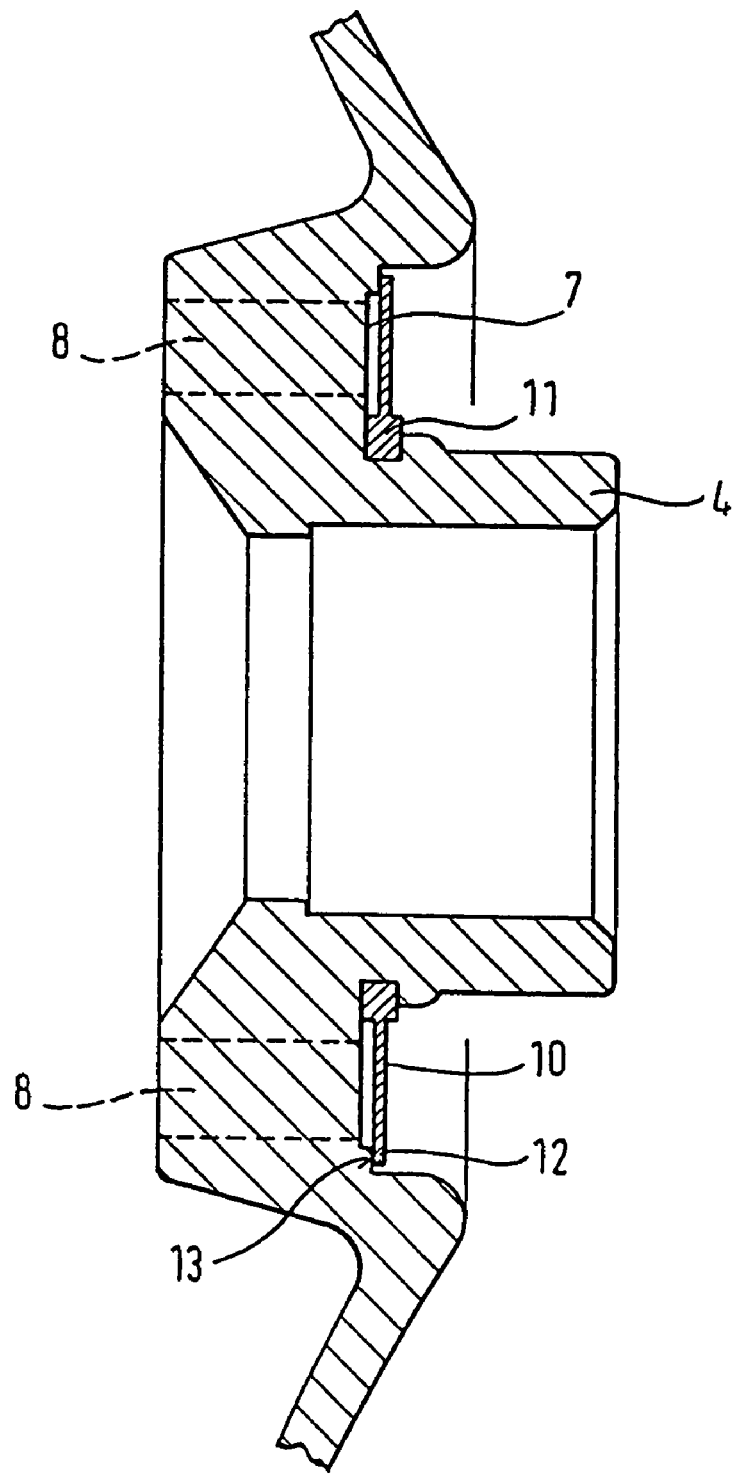
Figure 4:
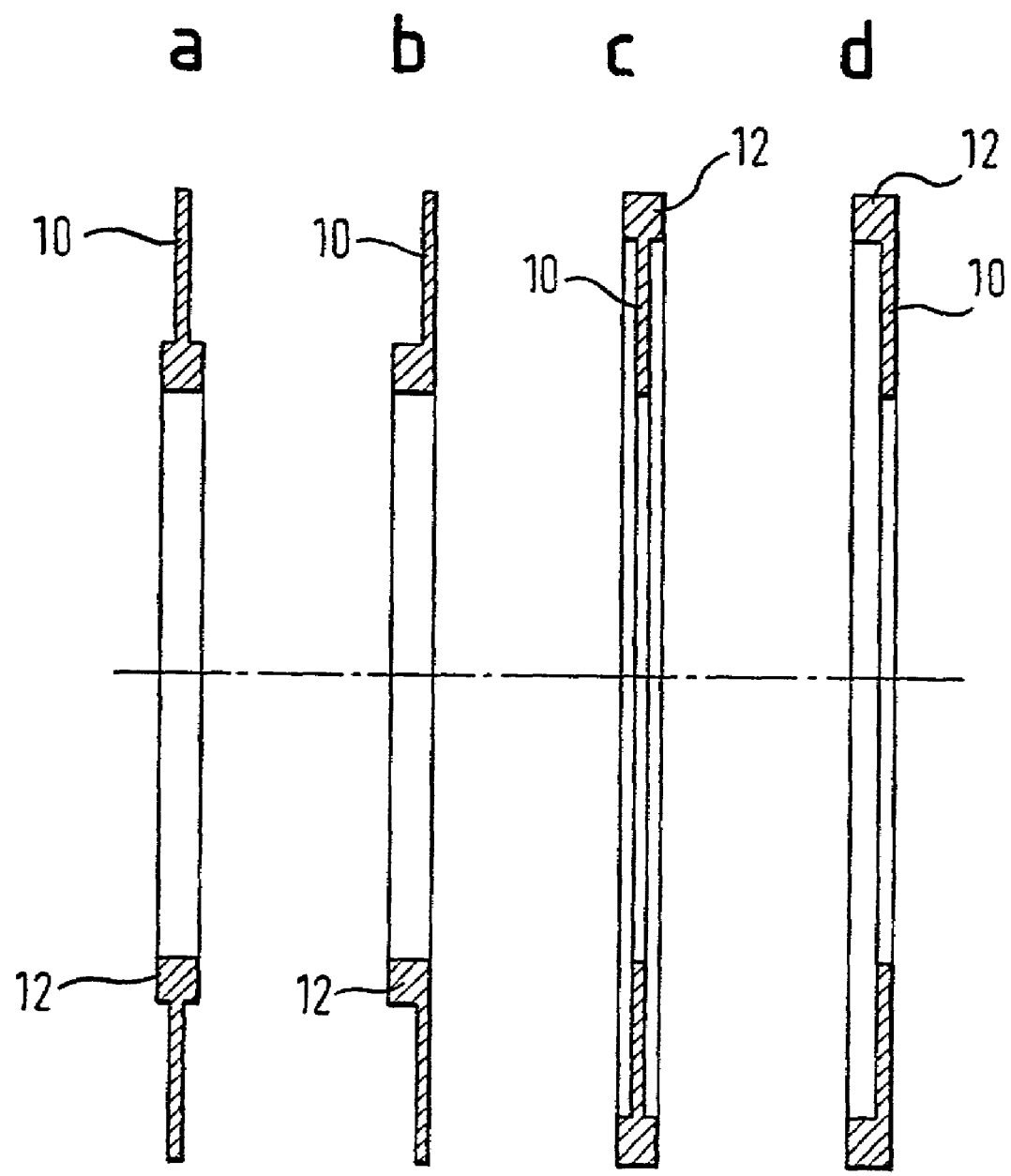

In FIG. 4 in a cross-sectional view are shown valve elements in different embodiments which can be used with the inhalation mask according to the invention. Here, FIG. 4a shows a valve element which at the inner edge comprises the section 12 of enlarged cross-section. The valve element according to FIG. 4a is also shown in FIG. 3. In both figures it can be seen that the flexible portion of the valve element 10 is arranged centrally to the section 12. Due to this symmetrical construction, assembly by the patient after cleaning is made easier. In the embodiment of the valve element in FIG. 4b, the flexible portion of the valve element is moved to the edge of the section 12 of enlarged cross-section. However, the section 12 is at the inner edge of the valve element in the embodiment in FIG. 4b too. In the embodiment in FIG. 4c the section 12 of enlarged cross-section is arranged at the outer edge of the valve element 10. According to this design, the groove for receiving the section 12 in the mask must be provided at the location at which the supporting edge 13 is formed in FIG. 3. Likewise correspondingly the supporting edge must be formed at the location of the mask at which in FIG. 3 the groove 9 is provided. The embodiment in FIG. 4d corresponds to the embodiment in FIG. 4b, but here too the section 12 of enlarged cross-section is arranged at the outer edge of the valve element. All the embodiments of the valve element shown in FIG. 4 for the inhalation mask according to the invention are rotationally symmetrical to the axis of rotation shown in FIG. 4.

Figure 5:
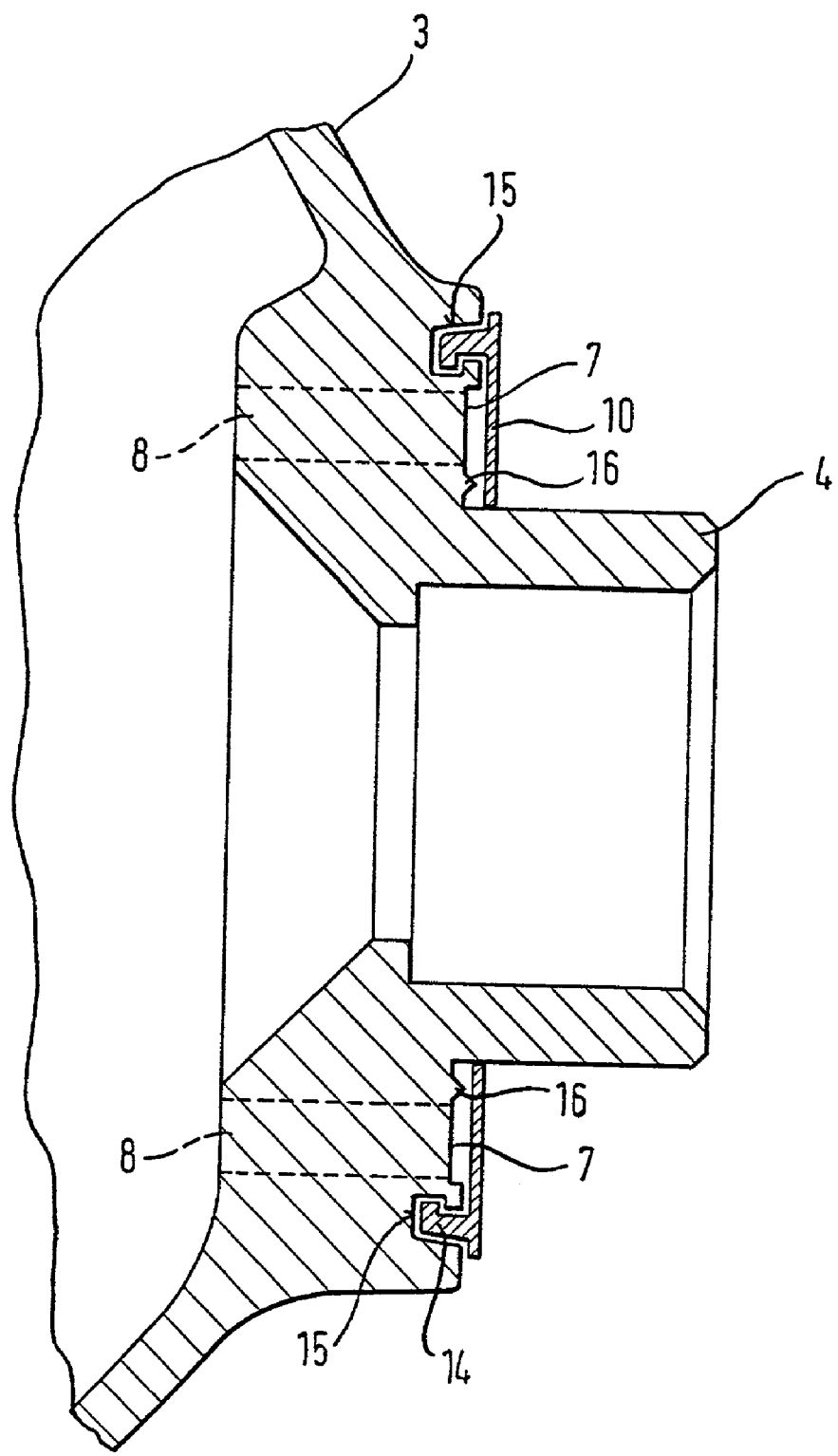

FIG. 5 shows a further embodiment of a valve element 10 according to the invention which is attached to the second mask region 3 of an inhalation mask according to the invention. The flat valve element 10 is of annular construction and arranged around the connecting socket 4 for a therapeutic nebuliser. The valve element 10 comprises a latch projection 14 which extends around in the vicinity of the outer edge of the valve element 10. In the second mask region 3 of the inhalation mask according to the invention shown in FIG. 5 is formed a latch groove 15 which extends around concentrically to the cylindrical connecting socket 5 and in which the latch projection 14 of the valve element 10 can be latched. Further, a sealing lip 16 is formed, which runs around the cylindrical connecting socket 4 and is arranged in the vicinity of the inner edge of the valve element 10. Between the latch groove 15 and the sealing lip 16 are located the breathing channels 8 whose breathing openings 7 are closed by the valve element 10 when the user wearing the mask breathes in. In this example too the latch projection 14 can be arranged in the vicinity of the inner edge of the valve element when the latch groove 15 is arranged correspondingly.

Under certain conditions it is sensible if during his treatment the patient breathes against an elevated exhalation resistance which is desirably adjustable.

Figure 6:
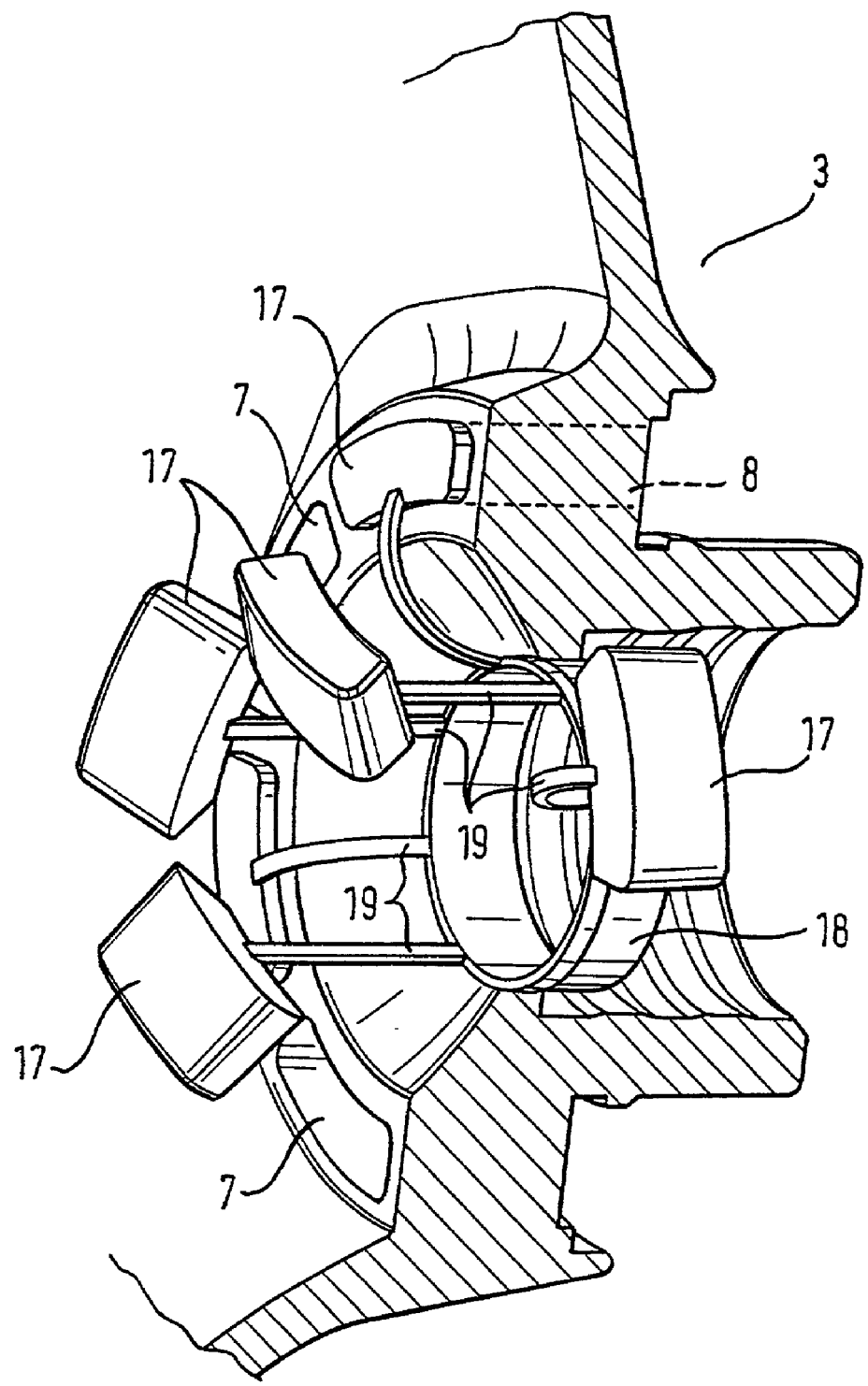

FIG. 6 shows the inhalation mask according to the invention with a closure device by means of which the effective cross-sectional area of the exhalation openings 7 can be influenced. The embodiment of the closure device shown in FIG. 6 includes one or more stoppers 17 whose size and shape are adapted to the exhalation openings 7 or the exhalation channels 8. Preferably, the stoppers 17 have a slight conical shape and can thus easily be inserted in the exhalation openings 7 or the breathing channels 8 and fixed. By the number of breathing openings 7 closed by means of the stoppers the effective total cross-sectional area of the breathing openings in an inhalation mask according to the invention is influenced. In this way an exhalation resistance which is preset for the user of the breathing mask according to the invention can be adjusted. As the stoppers 17 can be removed again as the closure device, the adjustment of the breathing resistance is variable in stages and adjustable to the user-dependent requirements. Stoppers 17 which only partially close the breathing channels 8 can also be provided. A similar effect is obtained by stoppers 17 which themselves comprise openings or breathing channels.

To facilitate handling of the closure device 17 in the form of one or more stoppers, in the embodiment of the closure device according to the invention shown in FIG. 6 is provided a holding device 18 to which the stoppers 17 of the closure device are connected by connecting elements 19. The connecting elements 19 are advantageously constructed in such a way that stoppers 17 which are not used can be detached, for example broken off, from the holding device 18. Preferably the stoppers 17, the holding device 18 and the connecting elements 19 are made from a material in one piece. The holding device 18 is ring-shaped so that it can be inserted in the cylindrical connecting socket 4 of the breathing mask according to the invention and supported there preferably on account of the selected dimensions (fit). However, in the connecting socket 4 of the inhalation mask can also be provided latch elements, for example a latch groove which extends around on the inner surface of the cylindrical connecting socket and whose width and depth are adapted to the dimensions of the holding ring 19.

Figure 7:
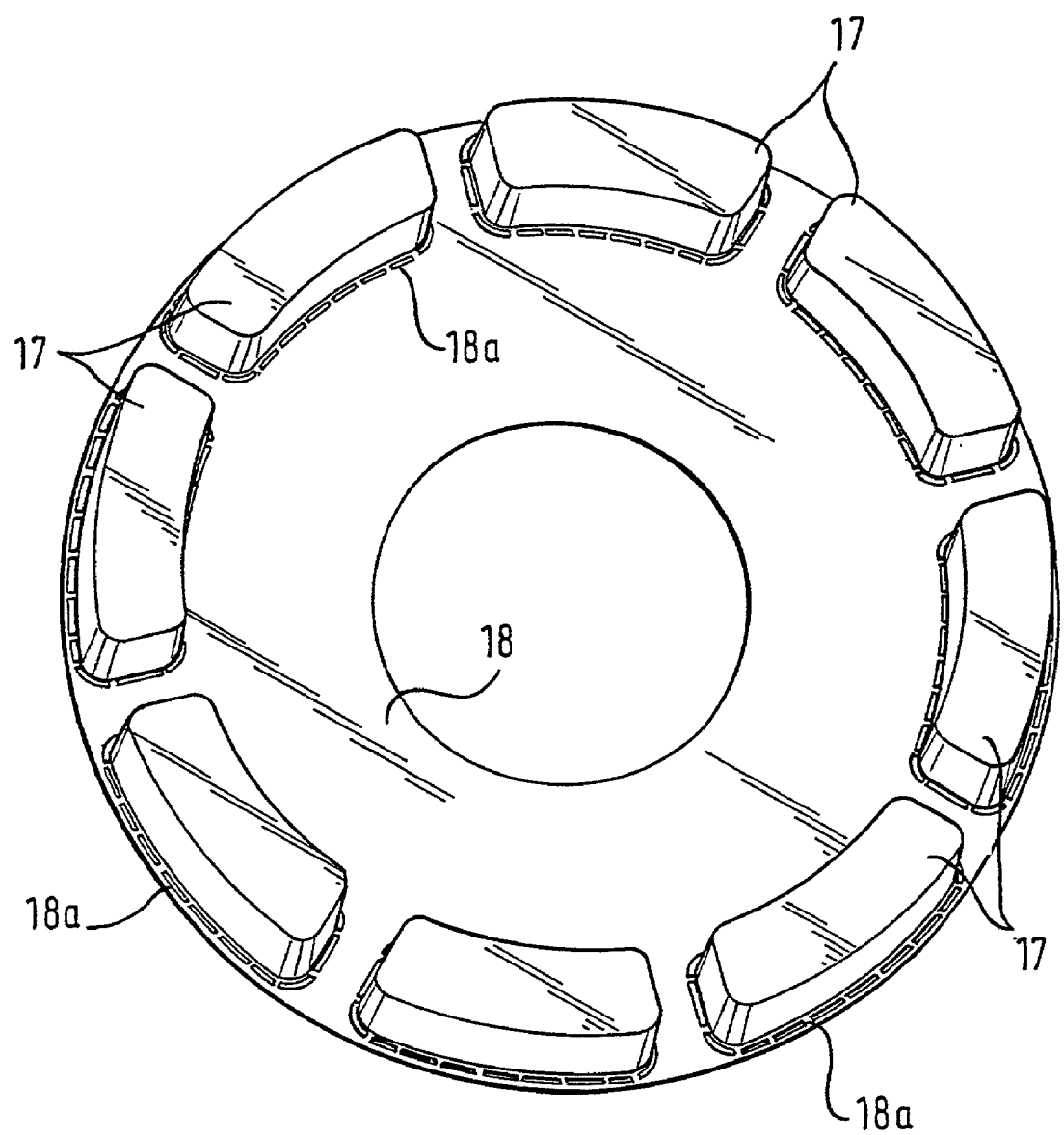

In FIG. 7 is shown a further embodiment of the closure device according to the invention comprising several stoppers 17 which can be inserted in the breathing channels of the therapeutic mask according to the invention. The stoppers 17 are in this embodiment held by a holding device 18 which on the one hand holds the stoppers 17 and on the other hand fixes the exact position of the stoppers 17, so that the latter can easily be introduced into the correspondingly arranged breathing channels 8 (cf. FIG. 6) of the therapeutic mask according to the invention. When the closure device shown in FIG. 7 is inserted in the breathing mask according to the invention, all the exhalation channels 8 are closed. To adjust the effective cross-sectional area, individual stoppers 17 can be detached from the holding device 18, as the stoppers can be broken out. For this purpose the stoppers 17 are each surrounded by a perforation 18a which allows each stopper 17 to be separated from the holding device 18.

The webs of the perforation 18a are to be regarded as connecting elements 19.

Figure 8:
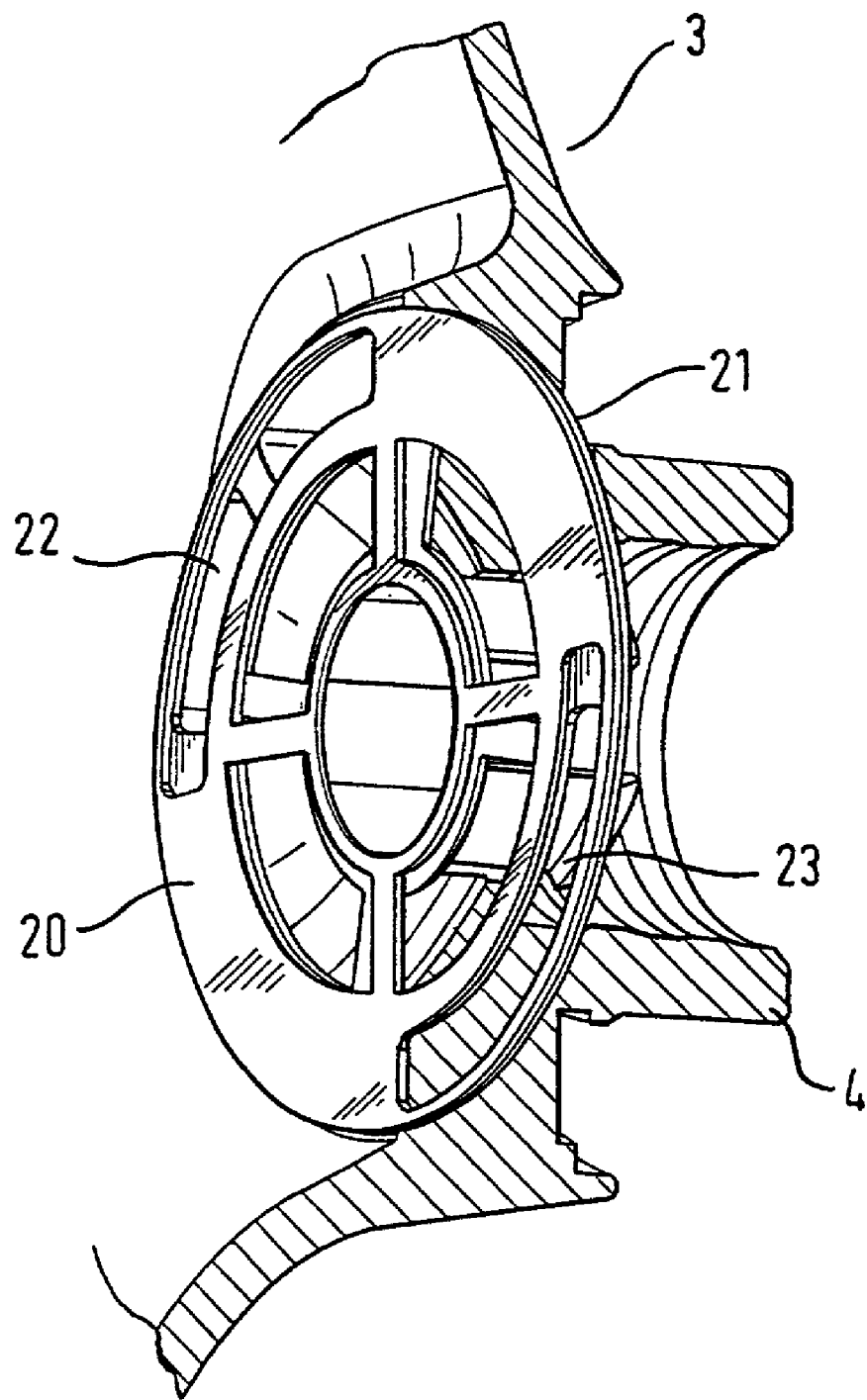

In FIG. 8 is shown a further embodiment of a closure device 20, 21 for an inhalation mask according to the invention. The closure device of this embodiment includes two flat annular discs 20 and 21 which are each provided with a number of openings 22. The two annular discs 20 and 21 lie one on top of the other and can be rotated relative to each other in such a way that the openings 22 lie one over the other to different degrees. Advantageously, the annular discs 20 and 21 comprise a marking which makes it easier for the user to align the annular discs with each other and hence align the openings with each other. In FIG. 8 is shown a rotational position in which the openings 22 overlap each other by about 95%. In this way a very large proportion of the maximum possible effective cross-sectional area is set for the exhalation openings 7. It can be seen from FIG. 8 that the two flat annular discs 20 and 21 can also be arranged relative to each other in such a way that the openings 22 lie exactly one over the other, so that the maximum effective cross-sectional area is set for exhalation. A rotational position of the two flat annular discs 20 and 21 in which the openings 22 are closed is not possible in the embodiment shown in FIG. 8, because complete closure of the exhalation openings 7 is normally not desirable, as the patient then breathes out into the connecting socket 4 for the therapeutic nebuliser and with the exhaled air can adversely affect production of the aerosol in the therapeutic nebuliser.

Figure 9:
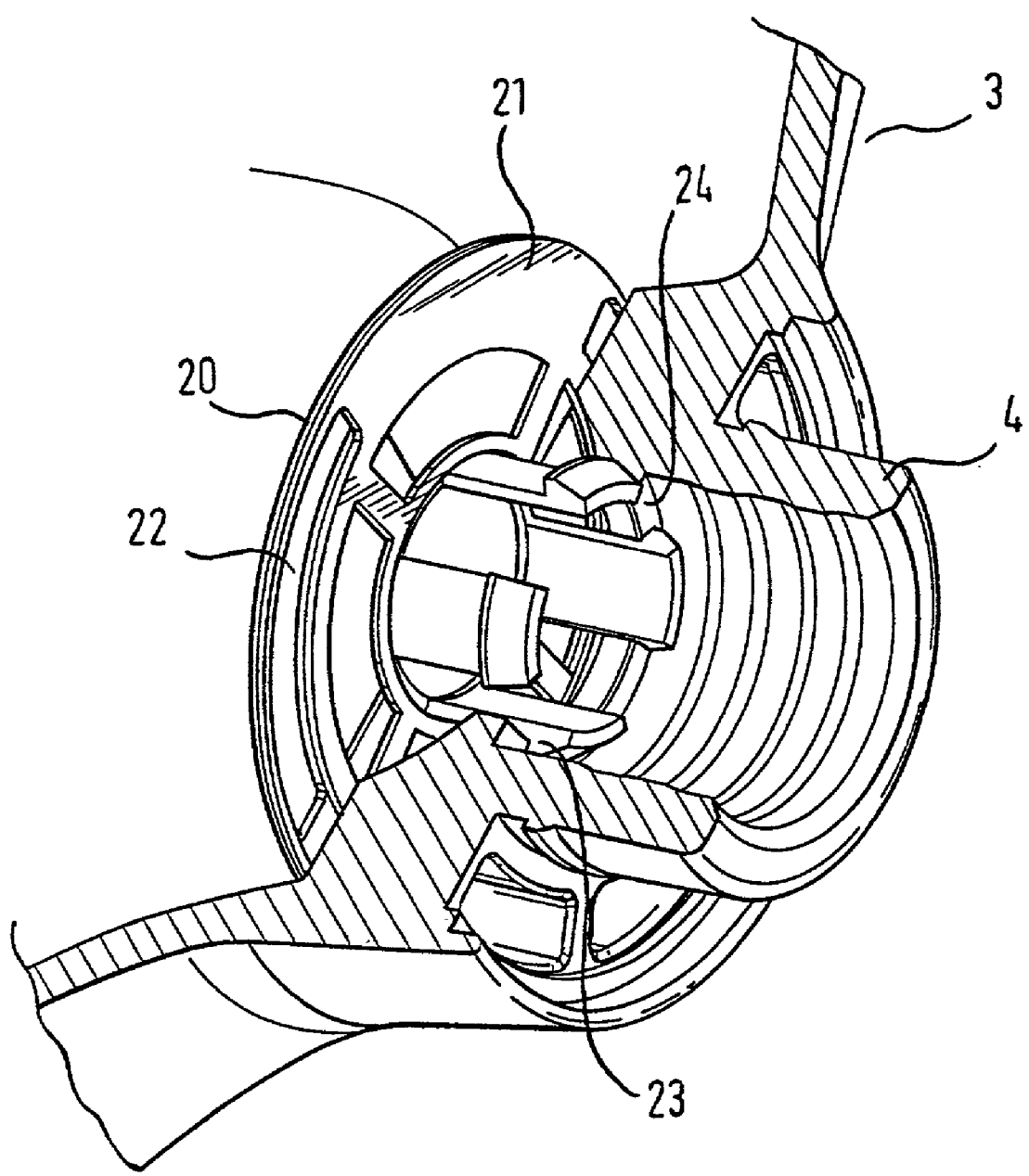

As shown in FIG. 9, one of the flat annular discs 20 is provided with holding lugs 23 which pass through an inner opening of the other flat annular disc 21 and can be inserted in the interior of the cylindrical connecting socket 4. As can be seen more clearly in FIG. 9, the holding lugs 23 in the inserted state are located behind a latch projection 24 which is formed on the inner surface of the cylindrical connecting socket 4. The latch projection 24 can be in the form of a peripheral latch groove. The holding lugs 23 of one flat annular disc 28 can however also be designed so as to be held in the interior of the cylindrical connecting socket 4 only on account of the suitably chosen dimensions (fit). In this case the holding lugs 23 can also be designed in the form of a holding cylinder or holding ring, similarly to the embodiment in FIG. 6. The construction shown in FIG. 8 is advantageous because rotation of one flat annular disc 20 relative to the other 21 is easier, because the holding lugs 23 do fix both flat annular discs in the axial direction, but build up a lower resistance for a rotational movement of one flat annular disc 20 or 21. By contrast, the design with a holding cylinder must preferably be effected in such a way that the second flat annular disc 21, which is fitted on the holding cylinder, is fixed relative to the holding cylinder on account of the chosen dimensions (fit) in a predetermined rotational position relative to the first flat annular disc 20 before the two flat annular discs 20 and 21 are fastened by means of the holding cylinder in the connecting socket 4 of the inhalation mask according to the invention.

The invention claimed is:

1. Inhalation mask, in particular for use with a therapeutic nebuliser, the mask comprising
   a main mask body (1) including a first region (2) configured for application of the mask to a human user's face, and a second region (3) which comprises:
      a connecting device (4) connected to the therapeutic nebuliser and
      a valve device comprising several exhalation openings (7) in the second region (3) of the mask body (1) which encircle the connecting device (4), and a valve element (10) which encircles the connecting device (4), wherein the valve element is used for closing exhalation openings (7) when the user wearing the mask breathes in and for opening the exhalation openings (7) when the user wearing the mask breathes out.

2. Inhalation mask according to claim 1, wherein the connecting device for a therapeutic nebuliser is a connecting socket.

3. Inhalation mask according to claim 2, wherein the connecting socket has a basic cylindrical shape.

4. Inhalation mask according to claim 1, wherein the exhalation openings (7) are formed by exhalation channels (8) which extend along the connecting device (4).

5. Inhalation mask according to claim 1, wherein the valve element (10) is annular.

6. Inhalation mask according to claim 5, wherein the annular valve element (10) at its inner edge or outer edge comprises a section (12) of enlarged cross-section which can be introduced into a groove (9) formed on the main mask body for supporting the annular valve element (10).

7. Inhalation mask according to claim 5, characterized in that the annular valve element (10) at its inner edge or outer edge comprises a latch projection (14) which can be latched in a latch groove (15) formed in the main mask body for supporting the annular valve element (10).

8. Inhalation mask according to claim 1, further comprising a closure device (17, 20, 21) for controlling the effective cross-sectional area of the exhalation opening (7).

9. Inhalation mask according to claim 8, characterized in that the closure device includes one or more stoppers (17) whose shape and size are adapted to the exhalation openings (7) or the exhalation channels (8) in such a way that they can be inserted in the exhalation openings (7) or the exhalation channels (8) and fixed.

10. Inhalation mask according to claim 9, characterized in that the stopper or stoppers (17) are connected to a holding device (18) by which the stoppers (17) can be fastened to the inhalation mask (1).

11. Inhalation mask according to claim 10, characterized in that the stoppers (17) are connected to the holding device (18) by connecting elements (19).

12. Inhalation mask according to claim 11, characterized in that the stoppers (17), the holding device (18) and the connecting elements (19) are made from a material in one piece.

13. Inhalation mask according to claim 8, wherein the closure device includes a first flat annular disc (20) and a second flat annular disc (21) located one on top of the other, each comprising one or more openings, the discs (20, 21) configured to sit in at least a first position and a second position relative to each other.

14. Inhalation mask according to claim 13, wherein the first flat annular disc (20) comprises holding lugs (23) which are arranged in an opening of the second flat annular disc (21) and which are latched in at the connecting device (4).

15. Inhalation mask according to claim 14, wherein the connecting device (4) comprises a latch projection (24) for engagement of the holding lugs (23) of the first flat annular disc (20).

16. Inhalation mask according to claim 13, wherein the first flat annular disc (20) comprises a holding cylinder which is arranged in an opening of the second flat annular disc (21) and which is inserted and supported in the connecting device (4).

17. Inhalation mask according to claim 13, wherein first and second flat annular discs (20, 21) include markings.

18. Inhalation mask, in particular for use with a therapeutic nebuliser, the mask comprising
    a main mask body including a first region (2) configured for application of the mask to a human user's face, and a second region (3), the second region comprising:
        (a) a connecting device (4) connected to the therapeutic nebuliser; and
        (b) a valve device comprising at least four exhalation openings (7) positioned in the second region (3) of the mask body positioned encircling the connecting device (4), and an annular valve element (10) in overlapping arrangement with the plurality of exhalation openings (7), the annular valve element (10) to positioned to encircle the connecting device (4).

19. Inhalation mask according to claim 18, further comprising a closure device (17. 20, 21) for controlling the effective cross sectional area of the plurality of exhalation openings (7), wherein the closure device includes a first flat annular disc (20) and a second flat annular disc (21) located one on top of the other, each comprising one or more openings, the discs (20, 21) configured to sit in at least a first position and a second position relative to each other.

20. Inhalation mask according to claim 19, wherein the first flat annular disc (20) comprises holding lugs (23) which are arranged in an opening of the second flat annular disc (21) and which are latched in at the connecting device (4).

21. Inhalation mask according to claim 20, wherein the connecting device (4) comprises a latch projection (24) for engagement of the holding lugs (23) of the first flat annular disc (20).

22. Inhalation mask according to claim 19, wherein the first flat annular disc (20) comprises a holding cylinder which is arranged in an opening of the second flat annular disc (21) and which is inserted and supported in the connecting device (4).

23. Inhalation mask according to claim 19, wherein first and second flat annular discs (20, 21) include markings.

24. Inhalation mask, in particular for use with a therapeutic nebuliser, the mask comprising
    a main mask body including a first region (2) configured for application of the mask to a human user's face, and a second region (3), the second region comprising:
        (a) a connecting device (4) connected to the therapeutic nebuliser; and
        (b) a valve device comprising a plurality of exhalation openings (7) positioned in the second region (3) of the mask body to encircle the connecting device (4), and an annular valve element (10) in overlapping arrangement with the plurality of exhalation openings (7), the annular valve element (10) to positioned to encircle the connecting device (4).

\* \* \* \* \*